United States Patent [19]
Pistor et al.

[11] B 4,014,914
[45] Mar. 29, 1977

[54] MANUFACTURE OF 4,4'-DIPHENYLMETHANE DIISOCYANATE AND A MIXTURE OF DIISOCYANATES AND POLYISOCYANATES

[75] Inventors: Hans Joachim Pistor, Walldorf; Herwig Hoffmann, Frankenthal; Hans-Ingo Joschek, Mannheim; Gotthilf Wenner, Ludwigshafen, all of Germany

[73] Assignee: Badische Anilin- & Soda-Fabrik Aktiengesellschaft, Ludwigshafen (Rhine), Germany

[22] Filed: Oct. 25, 1974

[21] Appl. No.: 518,076

[44] Published under the second Trial Voluntary Protest Program on March 30, 1976 as document No. B 518,076.

Related U.S. Application Data

[63] Continuation of Ser. No. 2,123, Jan. 12, 1970, abandoned.

[52] U.S. Cl. .............. 260/453 PH; 260/453 AM; 260/570 D
[51] Int. Cl.² .................................. C07C 119/02
[58] Field of Search ... 260/570 D, 453 AM, 453 PH

[56] References Cited

UNITED STATES PATENTS 3,542,871  11/1970  Thompson .................. 260/570

Primary Examiner—Lewis Gotts
Assistant Examiner—Dolph H. Torrence
Attorney, Agent, or Firm—Johnston, Keil, Thompson & Shurtleff

[57] ABSTRACT

Production of 4,4'-diphenylmethane diisocyanate and a mixture of diisocyanates and polyisocyanates by the phosgenation of pure 4,4'-diaminodiphenylmethane and a mixture of diamines and polyamines. 4,4'-Diaminodiphenylmethane is obtained by distillation of the mixture of products obtained from the reaction of aniline with formaldehyde and crystallization of the distillate from a solvent. The combined distillation residue and mother liquor from the crystallization form the mixture for reaction with phosgene to produce a mixture of diisocyanates and polyisocyanates. This process produces a highly pure 4,4'-diphenylmethane diisocyanate which is particularly suitable for the production of polyurethanes serving as intermediates in the manufacture of rigid foams or as glue.

6 Claims, 1 Drawing Figure

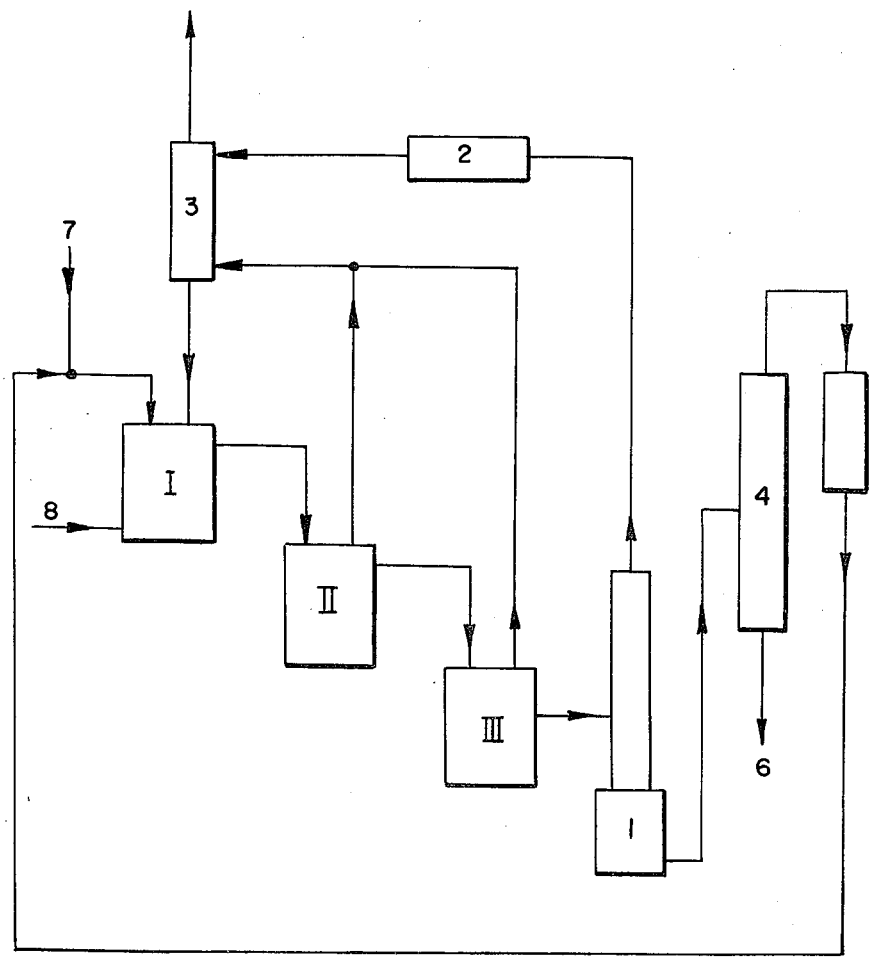
INVENTORS:
HANS JOACHIM PISTOR
HERWIG HOFFMANN
HANS-INGO JOSCHEK
GOTTHILF WENNER

MANUFACTURE OF 4,4'-DIPHENYLMETHANE DIISOCYANATE AND A MIXTURE OF DIISOCYANATES AND POLYISOCYANATES

This is a continuation of application Ser. No. 2,123, filed Jan. 12, 1970, and now abandoned.

The present invention relates to a process for the manufacture of 4,4'-diphenylmethane diisocyanate and a mixture of diisocyanates and polyisocyanates from diamines and polyamines obtained by condensing formaldehyde and aniline.

In industry there is an increasing demand for highly pure 4,4'-diphenylmethane diisocyanate and a mixture of diisocyanates and polyisocyanates of diamines and polyamines obtained by the condensation of aniline and formaldehyde. The diisocyanates are essentially the 4,4'-, 2,4'- and 2,2'-diphenylmethane diisocyanates, whilst the polyisocyanates are the isocyanates of higher condensation products of formaldehyde and aniline, for example triamines or tetramines. By triamine we mean, for example, the condensation product of three molecules of anilinne and two molecules of formaldehyde.

Whereas the mixture of diamines and polyamines necessary for the manufacture of a mixture of diisocyanates and polyisocyanates may be obtained relatively simply by the condensation of aniline and formaldehyde in the presence of catalytic quantities of hydrochloric acid, it is necessary to use an excess of aniline and stoichiometeric quantities of hydrochloric acid in the production of highly pure 4,4'-diamino-diphenymethane from aniline and formaldehyde. When stoichiometric quantities of hydrochloric acid are used, however, large quanitites of salt are produced on neutralization, which salt is very difficult to remove.

French Pat. No. 1,487,546 discloses the method of (a) producing a mixture of primary diamines and polyamines by condensing aniline and formaldehyde, (b) converting the resulting mixture to a mixture of diisocyanates and polyisocyanates by phosgenation and (c) distilling the mixture to obtain a 4,4'-diphenylmethane diisocyanate fraction and, as residue, a mixture of diisocyanates and polyisocyanates. The 4,4'-diphenylmethane diisocyanate obtained by this method contains, however, a relatively high proportion of isomeric diisocyanates and is therefore insufficiently pure for many applications.

We have now found that 4,4'-diphenylmethane diisocyanate and a mixture of diisocyanates and polyisocyanates may be conveniently produced by condensing formaldehyde with excess aniline in the presence of strong aqueous mineral acids at temperatures which are low at the start of the reaction but rise as the reaction proceeds, neutralizing the reaction mixture at the end of the reaction, separating the resultiing mixture of primary diamines and primary polyamines into 4,4'-diaminodiphenylmethane and a mixture of the remaining primary diamines and primary polyamines, phosgenating the 4,4'-diaminodiphenylmethane to form 4,4'-diphenylmethane diisocyanate and phosgenating the mixture of primary diamines and primary polyamines to form a mixture of diisocyantes and polyisocyanates, provided that the condensation of aniline and formaldehyde is conducted with these components in a molar ratio of 2:1 to 6:1, the temperature being 10° to 90°C at the start of the reaction rising to 80° to 150°C as the reaction proceeds, that the mixture obtained after neutralization and comprising diamines and polyamines is distilled to separate all or some of the diamines, that substantially pure 4,4'-diaminodiphenylmethane is recovered from the mixture of separated diamines by crystallization from a solvent, and that the pure 4,4'-diaminodiphenylmethane is phosgenated alone and the mixture of primary amines remaining after the diamines have been removed by distillation is combined with the amines remaining in the mother liquor from the crystallization and the combined diamines are also phosgenated, the phosgenation in both cases being by conventional methods to produce pure 4,4'-diisocyanato-diphenylmethane and a mixture of diisocyanates and polyisocyanates. Substantially pure 4,4'-diaminodiphenylmethane generally means a 4,4'-diaminodiphenylmethane having a purity of at least 95%, preferably at least 98% by weight.

This process produces a highly pure 4,4'-diphenylmethane diisocyanate, which is of excellent value for the production of polyurethane elastomers. The resulting mixture of diisocyanates and polyisocyanates is a highly suitable starting material for the production of rigid polyurethane foams and is a valuable bonding agent for use in glueing wood.

The preparation of the mixture of primary diamines and primary polyamines from aniline and formaldehyde is well known. The condensation is carried out with aniline and formaldehyde in a molar ration of 2 to 6, preferably 3 to 5. Condensation is effected in the presence of strong aqueous mineral acids such as sulfuric acid and, in particular, hydrochloric acid. For each mole of aniline there is generally used 0.02 to 0.3, preferably 0.1 to 0.2 equivalent of mineral acid. The formaldehyde may be used in polymeric form, for examples as trioxane or paraformaldehyde. We prefer, however, to use commercial aqueous formaldehyde solutions, such as 20 to 50% aqueous formaldehyde solutions by weight, for the condensation.

The reaction is initially conducted in the lower temperature range at temperatures between 10° and 90°C, preferably between 10° and 30°C, and it is completed in the higher temperature range of 80° to 150°C, preferably 80° to 140°C. It may be advantageous to remove a substantial proportion of the water from the reaction mixture by distillation before the reaction has been completed and to subject the remaining mixture to further reaction at temperatures above 100°C, preferably at 120° to 150°C.

The reaction mixture obtained on completion of the condensation is neutralized, preferably by using alkaline earth metal hydroxides, such as calcium hydroxide, and particularly alkali metal hydroxides, such as sodium hydroxide or potassium hydroxide. The hydroxides may be added as such, but generally they are used in the form of aqueous solution and/or suspensions, for instance in the form of 5 to 50%, preferably 10 to 30%, aqueous solutions and/or suspensions by weight.

After neutralization the resulting mixture of primary diamines and primary polyamides is conveniently separated from the aqueous layer as organic layer, which is then distilled to give initially excess aniline. The distillation residue is then subjected to fractional distillation, which gives all or a portion of the diamines.

Whether all or only a portion of the diamines is distilled off depends on the amount of 4,4'-diphenylmethane diisocyanate and the mixture of diisocyanates and polyisocyanates required. Generally, only a portion — about 40 to 90% by weight — of the total diamines is separated.

The separated mixture of diaminodiphenylmethanes is then separated by crystallization using a solvent, the 4,4'-diaminodiphenylmethane being obtained in crystalline form, whilst the isomers, such as 2.4'-diaminodiphenylmethane and 2,2'-diaminodiphenylmethane, remain in the mother liquor. Crystallization may be repeated a number of times if desired. Usually it is sufficient to recrystallize just once to produce a very pure product. Suitable solvents for the crystallization are, preferably, aromatic hydrocarbons containing one or two rings and one to three chlorine atoms, whilst aromatic hydrocarbons containing one or two alkyl groups, in particular methyl groups, are also suitable. Specific examples are 1-chloronaphthalene, trichlorobenzene, o-dichlorobenzne, toluene, xylene and, in particular, chlorobenzene. The most suitable ratio of solvent to the mixture of diaminodiphenylmethanes may be determined by simple experiment. Generally the amount of solvent used is 2 to 10 times and preferably 3 to 6 times the weight of the mixture of diaminodiphenylmethanes. It is advantageous to effect crystallization in a solvent of the type in which the phosgenation to form a mixture of diisocyanates and polyisocyanates is carried out.

Crystallization is carried out in known manner, for example by dissolving the diaminodiphenylmethanes in 2 to 10 times and preferably 3 to 6 times their weight of solvent applying heat to effect dissolution at, for example, 40° to 80°C, and then cooling to temperature between 20° and 30°C. The 4,4'-diaminodiphenylmethane which crystallizes out is conveniently removed from the solvent by filtration or by centrifuge.

The primary amines contained in the mother liquor may be isolated, for example by distillation, before they are combined with the mixture of primary amines left after separation of the diamines. We prefer, however, to combine the mother liquor as it is with the mixture of primary amines left as residue after separation of the diamines.

Phosgenation of the 4,4'-diaminodiphenylmethane to form 4,4'-diphenylmethane diisocyanate and of the mixture of primary diamines and primary polyamines is carried out in known manner, for example by the processes described in U.S. Pat. No. 2,683,730; J. Chem. Soc., 117, 998–992 (1920) and Ullmann's Enzyklopadie der Technischen Chemie, 9, pp. 8 et seq. (1957).

The amines are converted for instance by a continuous phosgenation procedure to isocyanates, for example using a 20% solution by weight and, if necessary, a number of stages, for example a cascade comprising three vessels equipped with stirrers, and using excess phosgene initially at low temperatures of preferably up to 30°C and subsequently temperatures of up to 170°C. The solvent, preferably chlorobenzene, is removed by distillation. In the case of mixture of diisocyanates and polyisocyanates the bottoms may be further processed with no intermediate treatment, whilst they will be redistilled if it is desired to obtain highly pure 4,4'-diphenylmethane diisocyanate.

The process of the invention is illustrated below with reference to the Example, in which the parts are by weight, unless otherwise stated, Parts by weight to parts by volume are as the kilogram to the liter.

EXAMPLE

Into a vessel equipped with stirrer there are fed 465 parts of aniline, 100 parts of 30%w/w aqueous formaldehyde solution and 50 parts of 36% w/w aqueous hydrochloric acid per hour with stirring and cooling to about 10°C. The vessel is connected by an overflow pipe to a vessel of 800 parts by volume capacity, in which the contents are maintained at about 100°C with stirring. The mean residence time of the reaction mixture in this vessel is about 1 hour. The reaction mixture leaves this vessel by overflowing into a film evaporator in which the water, and some aniline azeotropically are distilled and withdrawn at the top. The bottoms remaining after the withdrawal of the water are kept in a coil for 2 to 3 hours at a temperature of about 130°C until the condensation reaction is complete. Neutralization is effected by treating the reaction product with 100 parts of 20% w/w aqueous sodium hydroxide per hour, and the aqueous layer is separated from the organic layer, which is then washed with water, using, preferably, the water distilled off in the film evaporator. The organic layer is then fractionally distilled under reduced pressure to give 290 parts of aniline per hour at 20 mm, this recovered aniline being recycled. From the residue there is then separated 100 parts per hour of the mixture of diaminodiphenylmethanes having a boiling range of 220° to 230°C at 2 mm. The separated diaminodiphenylmethanes are dissolved in 400 parts of monochlorobenzene by heating, and the resulting solution is then cooled to 20°C, when 4,4'-diaminodiphenylmethane crystallizes out. The crystals are removed by filtration in a pan filter and then washed with 100 parts of cold chlorobenzene. There are thus obtained 50 parts of 4,4'-diaminodiphenylmethane, m.p. 92°C. The mother liquor and the chlorobenzene washings are combined and used for dissolving the bottom remaining after removal of the diaminodiphenylmethanes in the film evaporator. The resulting solution of primary diamines and primary polyamines is then phosgenated.

The apparatus for the phosgenation of the 4,4'-diaminodiphenylmethane or the mixture of diamines and polyamines comprises a cascade of three vessels provided with stirrers and operated at temperatures of 5°–10°C, 60°–80°C and 110°–130°C respectively (cf. accompanying Figure).

Whereas vessel I has a capacity of 1,000 parts by volume, vessel II has a capacity of 1,500 parts by volume and vessel III one of 2,500 parts of volume. The phosgenation apparatus is connected to a stripping column 1, in which the phosgene and some of the solvent are distilled off and, after being cooled in 2 and passing through a washing column 3, are recycled to the reactor I. In the washing column 3 the gases given off from vessels II and III are also washed to remove phosgene from said gases and recycle it. In a further column 4 the residual solvent is removed as was used to dissolve the primary diamines or primary polyamines fed to the vessel I, the isocyanates being obtained as crude products at 6. 80 Parts of diamine or diamine plus polyamine by weight and 330 parts of chlorobenzene by volume are fed to the apparatus sketched in the accompanying Figure per hour (at 7), whilst about 95 parts of phosgene by weight is passed into the vessel I at 8 as a gas or liquid. The stripping column is heated with sufficient steam to cause about 600 parts of phogene and chlorobenzene by volume to evaporate and to pass through the washing column back to vessel I to maintain a thinly liquid reaction mixture therein. About 100 parts of isocyanates are obtained in the base of the stripping column per hour, these still being dissolved in 330 parts of chlorobenzene by volume, from which they are separated in the fractionating column. In the case of the mixture of diisocyanates and polyisocyanates, the base product may be directly removed at 6 and processed further. But if highly pure 4,4'-diphenylmethane diisocyanate is the required product, this is again distilled off in a further evaporating plant and withdrawn from the top thereof. The yield of 4,4'-diphenylmethane diisocyanate and of the mixture of diisocyanates and polyisocyanates is in both cases approximately 100% on the primary amine used as starting material for phosgenation.

We claim:

1. A process for the manufacture of 4.4'-diphenylmethane diisocyanate and a mixture of diisocyanates and polyisocyanates which consists essentially of
    a. condensing aniline with formaldehyde in a molar ratio of from 2:1 to 6:1 in the presence of a strong aqueous mineral acid at temperatures of 10° to 90°C at the start of the reaction rising to temperatures ranging from 80° to 150°C as condensation proceeds;
    b. neutralizing the reaction mixture on completion of condensation;
    c. distilling off from the mixture obtained after neutralization all or a portion of the diamines;
    d. recovering substantially pure 4,4'-diaminodiphenylmethane from the mixture of separated diamines by crystallization from a solvent;
    e. combining the distillation residue from step (c) and the mother liquor from step (d);
    f. reacting the substantially pure 4,4'-diaminodiphenylmethane with phosgene to form 4,4'-diphenylmethane diisocyanate; and
    g. reacting the mixture from step (e) containing diamines and polyamines with phosgene to form a mixture of diisocyanates and polyisocyanates.

2. A process as set forth in claim 1 wherein about 40 to 90% by weight of the diamines are distilled off in step (c).

3. A process as set forth in claim 1 wherein the solvent used in step (c) is an aromatic compound having one or two rings and one or two chlorine atoms or an aromatic compound having one or two methyl groups.

4. A process as set forth in claim 1 wherein the solvent used in step (c) is chlorobenzene.

5. A process as set forth in claim 1 wherein the mineral acid is hydrochloric acid and wherein the amount of said acid is from 0.02 to 0.3 mole for each mole of aniline.

6. A process as set forth in claim 1 wherein the temperature in step (a) at the start of the reaction is from 10° to 30°C and wherein the temperature rises to from 80° to 140°C as condensation proceeds.

* * * * *